United States Patent
Schonenberg et al.

(10) Patent No.: US 11,051,766 B2
(45) Date of Patent: Jul. 6, 2021

(54) MODIFYING A PATIENT INTERFACE COMPUTER SYSTEM BASED ON AN EQUIVALENT EFFORT PARAMETER

(71) Applicant: KONINKLIJKE PHILIPS N.V., Eindhoven (NL)

(72) Inventors: Maartje Helena Schonenberg, Eindhoven (NL); Privender Kaur Saini, Veldhoven (NL); Lenneke Van Genugten, Eindhoven (NL); Mareike Klee, Straelen (DE); Rita Priori, Cambridge (GB); Marian Dekker, Oss (NL); Chevone Marie Barretto, London (GB); Wilhelmus Johannes Joseph Stut, Eindhoven (NL); Christian Andreas Tiemann, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 434 days.

(21) Appl. No.: 16/022,853

(22) Filed: Jun. 29, 2018

(65) Prior Publication Data
US 2019/0000401 A1    Jan. 3, 2019

Related U.S. Application Data

(60) Provisional application No. 62/527,076, filed on Jun. 30, 2017.

(51) Int. Cl.
*A61B 5/00* (2006.01)
*A61B 5/0205* (2006.01)
(Continued)

(52) U.S. Cl.
CPC ............ *A61B 5/743* (2013.01); *A61B 5/0022* (2013.01); *A61B 5/0205* (2013.01);
(Continued)

(58) Field of Classification Search
CPC ..... A61B 5/743; A61B 5/0022; A61B 5/0205; A61B 5/02405; A61B 5/1118;
(Continued)

(56) References Cited

U.S. PATENT DOCUMENTS 8,706,530 B2 * 4/2014 Ohnemus ............... G16H 50/30
                                                    705/3
2008/0300914 A1   12/2008 Karkanias

FOREIGN PATENT DOCUMENTS

WO     WO0234129 A1     5/2002
WO     WO2017032635 A1  3/2017

OTHER PUBLICATIONS

Garcia-Aymerich, J. et al., "Regular Physical Activity Reduces Hospital Admission and Mortality in Chronic Obstructive Pulmonary Disease: A Population Based Cohort Study", Thorax 2006;61:772-778.

(Continued)

*Primary Examiner* — Lindsey G Wehrheim

(57) ABSTRACT

The present disclosure pertains to a system for facilitating configuration modifications for a patient interface computer system based on an equivalent effort parameter. In some embodiments, the system obtains (i) one or more first measurements associated with a first subject, the first subject having a clinical coefficient, (ii) one or more second measurements associated with a second subject. The system determines (i) a first effort parameter based on the one or more first measurements, (ii) a second effort parameter based on the one or more second measurements, and (iii) an equivalent effort factor for the first subject based on the one or more first measurements, the one or more second measurements, and the clinical coefficient. The system causes a configuration of the patient interface computer system to be modified based on the equivalent effort factor.

15 Claims, 4 Drawing Sheets

(51) Int. Cl.
    A61B 5/024    (2006.01)
    A61B 5/11     (2006.01)
    G16H 40/63    (2018.01)
    G16H 20/30    (2018.01)
    A61B 5/08     (2006.01)
    A61B 5/145    (2006.01)
(52) U.S. Cl.
    CPC ........ *A61B 5/02405* (2013.01); *A61B 5/1118*
        (2013.01); *A61B 5/486* (2013.01); *A61B*
        *5/4866* (2013.01); *A61B 5/7267* (2013.01);
        *G16H 20/30* (2018.01); *G16H 40/63*
        (2018.01); *A61B 5/0816* (2013.01); *A61B*
        *5/112* (2013.01); *A61B 5/14542* (2013.01)
(58) Field of Classification Search
    CPC ..... A61B 5/486; A61B 5/4866; A61B 5/7267;
        A61B 5/0816; A61B 5/112; A61B
        5/14542; G16H 20/30; G16H 40/63
    See application file for complete search history.

(56) References Cited

OTHER PUBLICATIONS

Troosters, T. et al., "Physical Inactivity in Patients with COPD, A Controlled Multi-Center Pilot-Study", Respiratory Medicine(2010) 104, 1005-1011.

Arne, M. et al., "Physical Activity and Quality of Life in Subjects with Chronic Disease: Chronic Obstructive Pulmonary Disease Compared with Rheumatoid Arthritis and Diabetes Mellitus", Informa Healthcare, Scandinavian Journal of Primary Health Care, 2009; 27: 141-47.

Vorrink, S. NW. et al., "Level of Daily Physical Activity in Individuals with COPD Compared with Healthy Controls", Respiratory Research 2011, 12:33, pp. 1-8.

Troosters, T. et al., "Improving Physical Activity in COPD: Towards a New Paradigm", Respiratory Research 2013, 14:115.

Gimeno-Santos, E. et al., "Determinants and Outcomes of Physical Activity in Patients with COPD: A Systematic Review", Chronic Obstructive Pulmonary Disease, Thorax 2014; 69: 731-739.

Pitta, F. et al., "Characteristics of Physical Activities in Daily Life in Chronic Obstructive Pulmonary Disease", American Journal of Respiratory and Critical Care Medicine, vol. 171, issue 9, pp. 972-977, May 2005.

Geraedts, H. AE. et al., "Adherence to and Effectiveness of an Individually Tailored Home-Based Exercise Program for Frail Older Adults, Driven by Mobility Monitoring: Design of a Prospective Cohort Study", BMC Public Health 2014, 14:570.

Gosker, H.R. et al., "Striking Similarities in Systemic Factors Contributing to Decreased Exercise Capacity in Patients With Severe Chronic Heart Failure or COPD", Chest Journal, May 2003, vol. 123, Issue 5, pp. 1416-1424.

Pitta, F. et al., "Physical Activity and Hospitalization for Exacerbation of COPD", 2006; Chest, vol. 129, Issue 3, pp. 536-544, Mar. 2006.

\* cited by examiner

MODIFYING A PATIENT INTERFACE COMPUTER SYSTEM BASED ON AN EQUIVALENT EFFORT PARAMETER

CROSS-REFERENCE TO RELATED APPLICATIONS

This patent application claims the priority benefit under 35 U.S.C. § 119(e) of U.S. Provisional Application No. 62/527,076 filed on Jun. 30, 2017, the contents of which are herein incorporated by reference.

BACKGROUND

1. Field

The present disclosure pertains to a system and method for facilitating configuration modifications for a patient interface computer system based on an equivalent effort parameter.

2. Description of the Related Art

Patients affected by pulmonary and/or cardiac disease are recommended to perform physical activities to improve quality of life and reduce exacerbations and mortality; however, disease and the related symptoms including breathlessness and fatigue may pose an impediment to their physical activities. Such patients may become disappointed with what they can actively do themselves compared to healthy subjects and their former selves, pre-illness or in younger days. As such, they may become de-motivated and depressed and may decrease their physical activities. Although computer-assisted physical activity monitoring systems exist, such systems may not consider the effects of pulmonary and/or cardiac disease on the patients' physical activities. For example, prior art systems may obtain, display, and compare raw physiological parameters corresponding to patients affected by a pulmonary disease with healthy individuals without accounting for physical impediments caused by the disease. As such, such systems may not account for the strenuous physical exertion caused by the pulmonary disease. These and other drawbacks exist.

SUMMARY

Accordingly, one or more aspects of the present disclosure relate to a system configured to facilitate configuration modifications for a patient interface computer system based on an equivalent effort parameter. The system comprises one or more processors or other components. The one or more processors are configured by machine-readable instructions to: obtain one or more first measurements associated with a first subject with one or more first sensors, the one or more first sensors being configured to provide real-time signals conveying information indicating one or more physiological measurements of the first subject, the first subject having a clinical coefficient; obtain one or more second measurements associated with a second subject with one or more second sensors, the one or more second sensors being configured to provide real-time signals conveying information indicating one or more physiological measurements of the second subject; determine a first effort parameter based on the one or more first measurements associated with the first subject; determine a second effort parameter based on the one or more second measurements associated with the second subject; determine an equivalent effort factor for the first subject based on the one or more first measurements associated with the first subject, the one or more second measurements associated with the second subject, and the clinical coefficient, the equivalent effort parameter being indicative of a translation of the first effort parameter to the second effort parameter; and cause a configuration of the patient interface computer system to be modified based on the equivalent effort parameter.

Yet another aspect of the present disclosure relates to a method for facilitating configuration modifications for a patient interface computer system based on an equivalent effort parameter with a system. The system comprises one or more processors or other components. The method comprises: obtaining one or more first measurements associated with a first subject with one or more first sensors, the one or more first sensors being configured to provide real-time signals conveying information indicating one or more physiological measurements of the first subject, the first subject having a clinical coefficient; obtaining one or more second measurements associated with a second subject with one or more second sensors, the one or more second sensors being configured to provide real-time signals conveying information indicating one or more physiological measurements of the second subject; determining, with the one or more processors, a first effort parameter based on the one or more first measurements associated with the first subject; determining, with the one or more processors, a second effort parameter based on the one or more second measurements associated with the second subject; determining, with the one or more processors, an equivalent effort factor for the first subject based on the one or more first measurements associated with the first subject, the one or more second measurements associated with the second subject, and the clinical coefficient, the equivalent effort parameter being indicative of a translation of the first effort parameter to the second effort parameter; and causing, with the one or more processors, a configuration of the patient interface computer system to be modified based on the equivalent effort factor.

Still another aspect of present disclosure relates to a system for facilitating configuration modifications for a patient interface computer system based on an equivalent effort parameter. The system comprises: means for obtaining one or more first measurements associated with a first subject, the means for obtaining the one or more first measurements being configured to provide real-time signals conveying information indicating one or more physiological measurements of the first subject, the first subject having a clinical coefficient; means for obtaining one or more second measurements associated with a second subject, the means for obtaining the one or more second measurements being configured to provide real-time signals conveying information indicating one or more physiological measurements of the second subject; means for determining a first effort parameter based on the one or more first measurements associated with the first subject; means for determining a second effort parameter based on the one or more second measurements associated with the second subject; means for determining an equivalent effort factor for the first subject based on the one or more first measurements associated with the first subject, the one or more second measurements associated with the second subject, and the clinical coefficient, the equivalent effort parameter being indicative of a translation of the first effort parameter to the second effort parameter; and means for causing a configuration of the patient interface computer system to be modified based on the equivalent effort factor.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
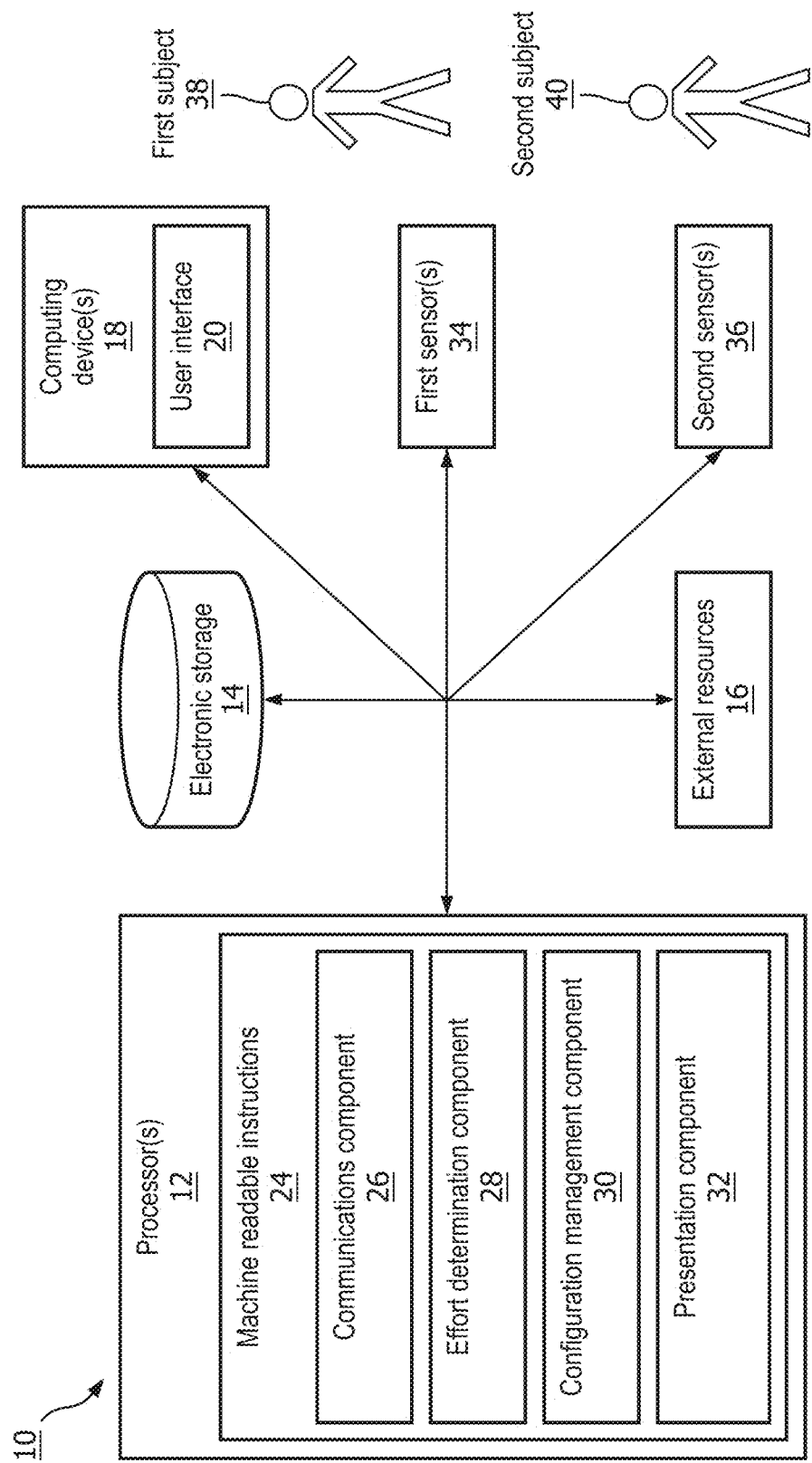
FIG. 1 is a schematic illustration of a system for facilitating configuration modifications for a patient interface computer system based on an equivalent effort parameter, in accordance with one or more embodiments.

As used herein, the singular form of "a", "an", and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic illustration of a system 10 for facilitating configuration modifications for a patient interface computer system based on an equivalent effort parameter. In some embodiments, system 10 is configured to motivate subjects affected by a condition (e.g., COPD, asthma, etc.) to be physically active. As such, system 10 is configured to put activities of the subjects affected by the condition into perspective by relating their physical activities effort to a comparable effort of a healthy subject, peers or loved ones. In some embodiments, system 10 is configured to monitor effort by determining physiological parameters of the subjects in various situations, a questionnaire, BORG scale of perceived exertion, and/or other methods. In some embodiments, system 10 is configured to translate an effort parameter corresponding to the subject affected by the condition to an effort parameter corresponding to a healthy individual. As an example, an effort parameter may be a quantitative measure of strenuous physical exertion. In some embodiments, the translated (i.e., equivalent) effort parameter corresponds to a matched effort parameter between subjects affected by a condition and healthy individuals. In some embodiments, system 10 effectuates, via a user interface, presentation of a retrospective and/or prospective comparison of the translated effort parameter and the effort parameter corresponding to the healthy individual. In some embodiments, system 10 comprises one or more processors 12, electronic storage 14, external resources 16, computing device 18, one or more first sensors 34, one or more second sensors 36, or other components.

In some embodiments, one or more first sensors 34 and one or more second sensors 36 are configured to provide real-time signals conveying information indicating one or more physiological measurements of first subject and second subject respectively. In some embodiments, one or more first sensors 34 and one or more second sensors 36 include one or more of pulse rate monitors, blood pressure monitors, blood oxygenation monitors (e.g., PPG sensor, SpO2 sensor), glucose monitors, thermometers, electrocardiogram (EKG) equipment, portable peak flow meters, portable spirometers, pedometers, tri-axial accelerometers, and/or other sensors. In some embodiments, one or more first sensors 34 and one or more second sensors 36 are implemented as one or more wearable devices (e.g., wrist watch, patch, Apple Watch, Fitbit, Philips Health Watch, etc.). In some embodiments, information from one or more first sensors 34 and one or more second sensors 36 may be automatically transmitted to computing device 18, one or more remote servers, or other destinations via one or more networks (e.g., local area networks, wide area networks, the Internet, etc.) on a periodic basis, in accordance to a schedule, or in response to other triggers.

Electronic storage 14 comprises electronic storage media that electronically stores information (e.g., one or more physiological measurements, demographics information, questionnaire responses, etc.). The electronic storage media of electronic storage 14 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 14 may be (in whole or in part) a separate component within system 10, or electronic storage 14 may be provided (in whole or in part) integrally with one or more other components of system 10 (e.g., computing device 18, processor 12, etc.). In some embodiments, electronic storage 14 may be located in a server together with processor 12, in a server that is part of external resources 16, in a computing device 18, and/or in other locations. Electronic storage 14 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 14 may store software algorithms, information determined by processor 12, information received via computing devices 18 and/or graphical user interface 20 and/or other external computing systems, information received from external resources 16, and/or other information that enables system 10 to function as described herein.

External resources 16 include sources of information and/or other resources. For example, external resources 16 may include look-up tables corresponding to objective parameters of a healthy subject while performing a particular activity (e.g., MET reference tables). In some embodiments, external resources 16 include health information related to first subject 38. In some embodiments, the health information comprises demographic information, vital signs information, medical condition information indicating medical conditions experienced by first subject 38, treatment information indicating treatments received by first subject 38, and/or other health information. In some embodiments, external resources 16 include contextual information including weather information, pollution information, pollen information, elevation information, and/or other information.

In some embodiments, external resources 16 include sources of information such as databases, websites, etc., external entities participating with system 10 (e.g., a medical records system of a health care provider that stores medical history information of patients), one or more servers outside of system 10, and/or other sources of information. In some embodiments, external resources 16 include components that facilitate communication of information such as a network (e.g., the internet), electronic storage, equipment related to Wi-Fi technology, equipment related to Bluetooth® technology, data entry devices, sensors, scanners, and/or other resources. External resources 16 may be configured to communicate with processor 12, computing device 18, electronic storage 14, and/or other components of system 10 via wired and/or wireless connections, via a network (e.g., a local area network and/or the internet), via cellular technology, via Wi-Fi technology, and/or via other resources. In some embodiments, some or all of the functionality attributed herein to external resources 16 may be provided by resources included in system 10.

Computing devices 18 are configured to provide an interface between first subject 38, second subject 40, and/or other users, and system 10. In some embodiments, individual computing devices 18 are and/or are included in desktop computers, laptop computers, tablet computers, smartphones, and/or other computing devices associated with individual caregivers 14, individual patients 12, and/or other users. In some embodiments, individual computing devices 18 are, and/or are included in equipment used in hospitals, doctor's offices, and/or other facilities. Computing devices 18 are configured to provide information to and/or receive information from first subject 38, second subject 40, and/or other users. For example, computing devices 18 are configured to present a graphical user interface 20 to first subject 38, second subject 40, and/or other users to facilitate entry and/or selection of information related to perceived fatigue, perceived exertion, degree of breathlessness, amount of coughing during and/or after performing an activity, and/or other subjective measures. In some embodiments, graphical user interface 20 includes a plurality of separate interfaces associated with computing devices 18, processor 12, and/or other components of system 10; multiple views and/or fields configured to convey information to and/or receive information from user 34, and/or other users; and/or other interfaces.

In some embodiments, computing devices 18 are configured to provide user interface 20, processing capabilities, databases, or electronic storage to system 10. As such, computing devices 18 may include processor 12, electronic storage 14, external resources 16, or other components of system 10. In some embodiments, computing devices 18 are connected to a network (e.g., the internet). In some embodiments, computing devices 18 do not include processor 12, electronic storage 14, external resources 16, or other components of system 10, but instead communicate with these components via the network. The connection to the network may be wireless or wired. For example, processor 12 may be located in a remote server and may wirelessly cause presentation of the one or more predictions via the user interface to a care provider on computing devices 18 associated with that caregiver (e.g., a doctor, a nurse, a central caregiver coordinator, etc.).

Examples of interface devices suitable for inclusion in user interface 20 include a camera, a touch screen, a keypad, touch sensitive or physical buttons, switches, a keyboard, knobs, levers, a display, speakers, a microphone, an indicator light, an audible alarm, a printer, tactile haptic feedback device, or other interface devices. The present disclosure also contemplates that computing devices 18 includes a removable storage interface. In this example, information may be loaded into computing devices 18 from removable storage (e.g., a smart card, a flash drive, a removable disk, etc.) that enables caregivers or other users to customize the implementation of computing device 18. Other exemplary input devices and techniques adapted for use with Computing devices 18 or the user interface include an RS-232 port, RF link, an IR link, a modem (telephone, cable, etc.), or other devices or techniques.

Processor 12 is configured to provide information processing capabilities in system 10. As such, processor 12 may comprise one or more of a digital processor, an analog processor, a digital circuit designed to process information, an analog circuit designed to process information, a state machine, or other mechanisms for electronically processing information. Although processor 12 is shown in FIG. 1 as a single entity, this is for illustrative purposes only. In some embodiments, processor 12 may comprise a plurality of processing units. These processing units may be physically located within the same device (e.g., a server), or processor 12 may represent processing functionality of a plurality of devices operating in coordination (e.g., one or more servers, computing device 18, devices that are part of external resources 16, electronic storage 14, or other devices.)

In some embodiments, processor 12, external resources 16, computing devices 18, electronic storage 14, one or more first sensors 34, one or more second sensors 36, and/or other components may be operatively linked via one or more electronic communication links. For example, such electronic communication links may be established, at least in part, via a network such as the Internet, and/or other networks. It will be appreciated that this is not intended to be limiting, and that the scope of this disclosure includes embodiments in which these components may be operatively linked via some other communication media. In some embodiments, processor 12 is configured to communicate with external resources 16, computing devices 18, electronic storage 14, and/or other components according to a client/server architecture, a peer-to-peer architecture, and/or other architectures.

As shown in FIG. 1, processor 12 is configured via machine-readable instructions 24 to execute one or more computer program components. The computer program components may comprise one or more of a communications component 26, an effort determination component 28, a configuration management component 30, a presentation component 32, or other components. Processor 12 may be configured to execute components 26, 28, 30, or 32 by software; hardware; firmware; some combination of software, hardware, or firmware; or other mechanisms for configuring processing capabilities on processor 12.

It should be appreciated that although components 26, 28, 30, and 32 are illustrated in FIG. 1 as being co-located within a single processing unit, in embodiments in which processor 12 comprises multiple processing units, one or more of components 26, 28, 30, or 32 may be located remotely from the other components. The description of the functionality provided by the different components 26, 28, 30, or 32 described below is for illustrative purposes, and is not intended to be limiting, as any of components 26, 28, 30, or 32 may provide more or less functionality than is described. For example, one or more of components 26, 28, 30, or 32 may be eliminated, and some or all of its functionality may be provided by other components 26, 28, 30, or 32. As another example, processor 12 may be configured to execute one or more additional components that may perform some or all of the functionality attributed below to one of components 26, 28, 30, or 32.

Communications component 26 is configured to obtain one or more first measurements associated with first subject 38 with one or more first sensors 34 during a first time period. In some embodiments, first subject 38 is healthy (e.g., no clinical conditions). In some embodiments, first subject 38 is affected by a first condition. In some embodiments, first subject 38 is affected by a first severity of the first condition. In some embodiments, first subject 38 affected by the first condition may exhibit a sedentary lifestyle and/or lower physical activity. In some embodiments, the first condition includes Chronic Obstructive Pulmonary Disease (COPD), emphysema, asthma, heart failure, cardiovascular diseases, hypertension and/or other conditions. In some embodiments, first subject 38 may be and/or be a part of a population (e.g., post-rehab group).

In some embodiments, communications component 26 is configured to obtain one or more second measurements associated with second subject 40 with one or more second sensors 36 during the first time period. In some embodiments, second subject 40 is healthy (e.g., no clinical conditions). In some embodiments, second subject 40 is affected by a second severity of the first condition, the second severity being (i) similar to or (ii) different from the first severity. In some embodiments, second subject 40 is not affected by the first condition. For example, second subject may include a healthy subject (e.g., with average health, fit individual, athlete, etc.). In some embodiments, second subject 40 may be and/or be a part of a population (e.g., a group of athletes). In some embodiments, second subject 40 may be represented by one or more health metrics that characterize an average healthy person (e.g., MET data). As such, a single subject may be compared with an average healthy person via the Compendium of Physical Activities.

In some embodiments, the one or more first measurements and the one or more second measurements are associated with the same activity (e.g., running). In some embodiments, the one or more first measurements and the one or more second measurements are associated with different activities (e.g., gardening or household activities for a COPD patient could be identical in effort to jogging for a healthy person).

In some embodiments, communications component 26 is configured to continuously obtain the one or more first measurements and the one or more second measurements (e.g., on a periodic basis, in accordance with a schedule, or based on other automated triggers).

In some embodiments, the one or more physiological measurements associated with first subject 38 and/or the one or more physiological measurements associated with second subject 40 include one or more of a heart rate, a breathing rate, a heart rate percentage, a heart rate reserve, a calorie expenditure, a blood oxygen saturation level, maximum volume of oxygen, a number of steps taken, cardiac cycle, energy expenditure and/or other measurements.

In some embodiments, communications component 26 is configured to obtain subjective data associated with first subject 38 and second subject 40. In some embodiments, the subjective data includes an assessment of what the subject, family, or care provider perceives to be the condition, health status, and/or problem. In some embodiments, the subjective data includes one or more of perceived fatigue, perceived exertion (e.g., Borg scale), degree of breathlessness, amount of coughing during and/or after performing an activity, and/or other data. By way of a non-limiting example, communications component 26 may obtain the subjective data via a questionnaire provided on user interface 20 during and/or after the activity.

In some embodiments, communications component 26 is configured to obtain demographics information associated with first subject 38 and second subject 40. In some embodiments, the demographics information includes one or more of an age, a gender, and/or other information. In some embodiments, communications component 26 is configured to obtain one or more co-morbidities (e.g., diabetes, kidney failure, anemia, etc.) associated with first subject 38.

In some embodiments, communications component 26 is configured to obtain contextual information associated with first subject 38, second subject 40, and/or other subjects. In some embodiments, the contextual information comprises one or more a weather condition, an amount of pollen present in the atmosphere, a pollution of the atmosphere, an elevation of the geographical area associated with first subject 38, second subject 40, and/or other subjects.

Effort determination component 28 is configured to determine a first effort parameter based on the one or more first measurements, the subjective data, the contextual information, and/or other information associated with first subject 38. In some embodiments, the first activity includes one or more of biking, hiking, swimming, climbing, rowing, dancing, activities of daily living (ADL), such as shopping or household chores, and/or other activities. For example, the first effort parameter may include a Metabolic Equivalent of Task (MET). In some embodiments, the MET is indicative of an energy cost of the first activity. In some embodiments, each liter of $O_2$ consumed by first subject 38 corresponds to a rate of energy expenditure. In some embodiments, effort determination component 28 may utilize a well-established relationship (e.g., linear and/or other correlations) between 02 consumption and heart-rate. In some embodiments, effort determination component 28 is configured to (i) determine a volume of $O_2$ consumed by first subject 38 based on a heart rate of subject 38 and, since 1 MET is equivalent to 3.5 ml $O_2$/kg/min, (ii) determine a MET parameter based on the determined volume of $O_2$ consumed by first subject 38. In some embodiments, effort determination component 28 is configured to (i) determine an energy expenditure of first subject 38, and, since 1 MET is equivalent to 1 kcal/kg/h, (ii) determine a MET parameter based on the determined energy expenditure of first subject 38.

In some embodiments, effort determination component 28 is configured to determine a second effort parameter based on (i) the one or more second measurements associated with second subject 40, (ii) reference health data associated with an average healthy person (e.g., via MET data table), and/or (iii) other information. In some embodiments, the second effort parameter may include a MET.

In some embodiments, effort determination component 28 is configured to obtain, from communications component 26, two measurements of Active Energy Expenditure (AEE) for first subject 38 and second subject 40. In some embodiments, the first measurement of AEE for first subject 38 includes a measurement obtained at rest. In some embodiments, the second measurement of AEE for first subject 38 includes a measurement obtained when performing what would be considered a high intensity level activity for first subject 38. In some embodiments, effort determination component 28 is configured to determine a change in AEE between rest and during the high intensity activity (e.g., $\Delta AEE_{COPD}$). In some embodiments, the first measurement of AEE for second subject 40 includes a measurement obtained at rest. In some embodiments, the second measurement of AEE for second subject 40 includes a measurement obtained when performing a high intensity level activity (e.g. running). In some embodiments, effort determination component 28 is configured to determine a change in AEE between rest and during the high intensity activity (e.g., $\Delta AEE_{Heathly}$).

In some embodiments, effort determination component 28 is configured to map one or more subjective ratings of exercise intensity to MET. For example, MET values less than 3 may be indicative of light intensity, MET values between 3 and 6 may be indicative of moderate intensity, and MET values greater than 6 may be indicative of vigorous intensity.

In some embodiments, effort determination component 28 facilitates comparing, based on the Borg Scale of Perceived Exertion, a cluster of healthy subjects with a cluster of subjects with a certain condition. For example, the perceived effort for a similar activity (e.g. walking), for a similar energy expenditure, may be compared between the cluster of healthy subjects and the cluster of subjects with the certain condition.

In some embodiments, effort determination component 28 is configured to determine an equivalent effort factor for first subject 38 based on the one or more first measurements associated with the first subject, the one or more second measurements associated with the second subject, a clinical coefficient (described below), and/or other factors. In some embodiments, the equivalent effort parameter is indicative of a translation of the first effort parameter to the second effort parameter. In some embodiments, the equivalent effort factor is one or more of a Metabolic Equivalent of Task (MET), a Training Impulse (TRIMP), a fraction of maximal heart rate, a fraction of heart rate reserve, an energy expenditure, a Borg scale of perceived exertion, and/or other parameters. For example, 30 minutes of walking for a COPD patient may be equivalent to 90 minutes of jogging for a healthy individual. As another example, a 1 km walk for a COPD patient may be equivalent to a 5 km walk for a healthy individual. In yet another example, 60 minutes of walking for a healthy individual may be equivalent to 120 minutes of walking for a COPD patient. In some embodiments, the equivalent effort parameter is and/or related to the MET. For example, the equivalent effort parameter may be a conversion of a MET associated with a particular activity for a healthy individual. For example, first subject 38, a COPD patient, may walk 5 km/h and the first measurements may be indicative of a MET of 9. In this example, the MET score of 9 may be compared to running at approximately 9-10 km/h for the average healthy person (e.g., second subject 40 and/or other healthy subjects).

In some embodiments, effort determination component 28 is configured such that the equivalent effort factor (EEF) is derived based on the active energy expenditure from first subject 38, second subject 40, and/or other subjects. In some embodiments, responsive to first subject 38 having a clinical condition, effort determination component 28 is configured to obtain, from communications component 26, a clinical coefficient $\beta_{DSC}$ (e.g., disease severity coefficient) which compensates for the limitations of the chronic condition. In some embodiments, the clinical coefficient may be based on one or more of a respiratory rate, a blood pressure, a heart rate, spirometry, oxygen saturation levels, neural respiratory drive, Dyspnoea scores, CAT, and/or other parameters. In some embodiments, the clinical coefficient is (i) determine by a healthcare provider, (ii) obtained from electronic storage 14, (iii) obtained from external resources 16 (e.g., first subject 38's electronic medical records), and/or obtained by other methods. In some embodiments, effort determination component 28 is configured to determine the equivalent effort factor by determining a product of the clinical coefficient and a quotient of the first effort parameter and the second effort parameter.

For example, $\beta_{DSC}$ may be 3.5; $\Delta AEE_{COPD}$ may be 20 ($AEE_{COPD\_meas1}$: patient at rest, $AEE_{COPD\_meas2}$: patient walking up the stairs); and $\Delta AEE_{Healthy}$ may be 50 ($AEE_{Heathly\_meas1}$: subject at rest, $AEE_{Healthy\_meas2}$: subject running at 3 m/s). In this example, $\beta_{DSC} \times \Delta AEE_{COPD} = EEF \times \Delta AEE_{Healthy}$. As such, $\beta_{DSC} \times (\Delta AEE_{COPD}/\Delta AEE_{Healthy}) = EFF$. Therefore, EFF is equivalent to 1.4 which indicates that the equivalent effort of COPD patient walking up the stairs is 1.4 times that of the healthy subject running 3 m/s compared to at rest.

Figure 2:
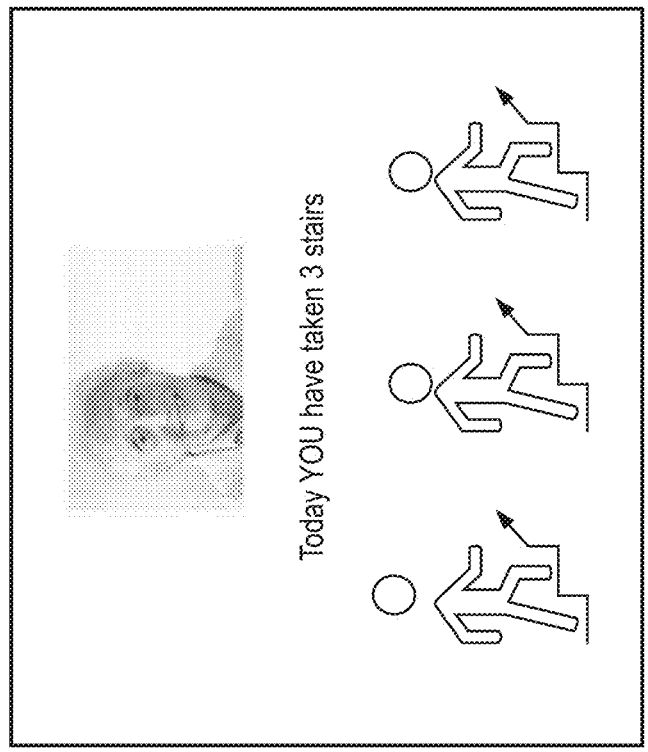
FIG. 2 illustrates effort comparison between a first subject and a second subject based on demographics information, in accordance with one or more embodiments.
Figure 2:
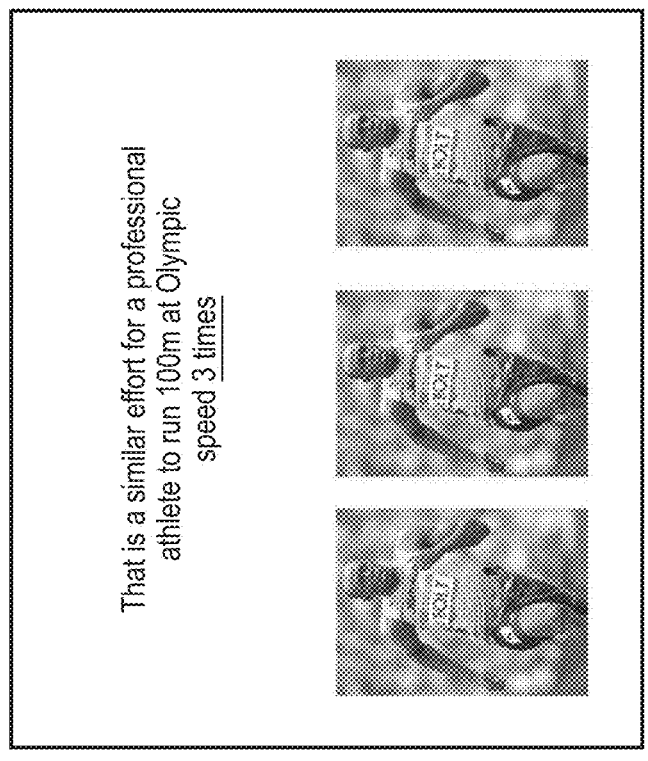

In some embodiments, effort determination component 28 is configured to incorporate demographics information associated with first subject 38, disease information associated with first subject 38, contextual information associated with first subject 38, and/or other information in the determination of the equivalent effort factor. By way of a non-limiting example, FIG. 2 illustrates effort comparison between a first subject and a second subject based on demographics information, in accordance with one or more embodiments. As shown in FIG. 2, an effort required for traveling three flights of stairs by an older individual may be equivalent to an effort for a professional athlete to run 100 meters at Olympics speed three times.

In some embodiments, effort determination component 28 may be and/or include a prediction model. As an example, the prediction model may include a neural network or other prediction model (e.g., machine-learning-based prediction model or other prediction model) that is trained and utilized for determining the first effort parameter, the second effort parameter, the equivalent effort parameter, and/or other parameters (described above). As an example, if a neural network is used, the neural network may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function which combines the values of all its inputs together. In some embodiments, each connection (or the neural unit itself) may have a threshold function such that the signal must surpass the threshold before it is allowed to propagate to other neural units.

These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free-flowing, with connections interacting in a more chaotic and complex fashion. By way of a non-limiting example, effort determination component 28 may map the first effort parameter to the second parameter score and vice versa. As another example, effort determination component 28 may determine different activities associated with the first effort parameter, the second effort parameter, and/or other parameters.

In some embodiments, effort determination component 28 is configured to determine second effort parameter for second subject 40 and/or other healthy subjects via $VO_2$ Estimation Method Based on Heart Rate Measurement by Firstbeat Technologies (https://www.firstbeat.com/app/uploads/2015/10/white_paper_vo2_estimation.pdf). In some embodiments, effort determination component 28 is configured to integrate, via the neural networks and/or machine learning, additional parameters related to a clinical condition in the determination and/or adjustment of the second effort parameter. Such clinical conditions may include categorical variables resulting in an additional offset or scaling when the second subject 40 and/or other healthy subject have the clinical condition. In some embodiments, more complex parameters, e.g., related to the severity of the condition are incorporated in the determination of the second effort parameter. In some embodiments, network weights are learned such that the perceived effort annotations from second subject 40 and/or other healthy subjects optimally match with the neural network output.

In some embodiments, effort determination component 28 is configured to update the prediction model based on (i) real-time feedback data including real-time data corresponding to the one or more first measurements, the one or more second measurements, and/or other measurements, (ii) historical information corresponding to the one or more first measurements, the one or more second measurements, and/or other measurements, or (iii) other information (e.g., other quantitative and/or subjective information described herein). As an example, the prediction model may be used to facilitate comparison of participants having widely differing health statuses. In this example, the prediction models may be configured such that first subject 38 has a chance of keeping up with second subject 40 by automatically updating the goal for first subject 38 based on real-time physiological measurements.

In some embodiments, effort determination component 28 is configured to (i) map, via $VO_2$ estimation, the first subject 38's heart rate to MET, (ii) determine a quotient of the determined MET and the equivalent effort factor, and (iii) determine, based on the determined quotient value and The Compendium of Physical Activities (e.g., a list of physical activities and corresponding MET values for the average healthy person) different activities for a similar effort.

Returning to FIG. 1, configuration management component 30 is configured to cause a configuration of a patient interface computer system (e.g., user interface 20, computing device 18, etc.) to be modified based on the equivalent effort factor. In some embodiments, configuration management component 30 is configured to motivate first subject 38, second subject 40, and/or other subjects to make progress by working towards a certain goal. For example, configuration management component 30 may be configured to determine whether first subject 38, second subject 40, and/or other subjects are interested to and/or are able to do an activity that compares to a well-known objective in a specific time frame, e.g. doing an activity comparable to a marathon run in a predetermined number of weeks, depending on the current activity level. In some embodiments, responsive to an affirmative indication by first subject 38, second subject 40, and/or other subjects to an activity goal, configuration management component 30 is configured to automatically set up a plan. In some embodiments, the plan includes a day by day set of activities of sufficient effort for the first subject 38, second subject 40, and/or other subjects. In some embodiments, configuration management component 30 is configured to monitor (i) the activity effort based on physiological measurements, subjective data, and/or other information and (ii) daily progress toward the goal. In some embodiments, configuration management component 30 is configured to adjust the plan if achievement becomes unrealistic.

In some embodiments, configuration management component 30 is configured to prospectively compare required efforts for first subject 38 and a reference healthy person (e.g., second subject 40, data obtained from MET tables indicative of an average healthy person, etc.). As such, configuration management component 30 may facilitate a mutual understanding of estimated effort of joint activities between first subject 38 and healthy individuals (e.g., second subject 40). For example, configuration management component 30 is configured to, for a given activity (e.g., walk or grocery shopping), determine: (i) how much larger the burden of the activity is for first subject 38 compared to second subject 40 (e.g., his/her spouse); (ii) in contrast to second subject 40's point of view, an equivalent length (e.g., walking distance) for first subject 38 based on the given activity's length; (iii) in contrast to first subject 38's point of view, an equivalent duration (e.g., running pace) for second subject 40 based on the given activity's pace; and (iv) the given activity's contribution to the goal for first subject 38, second subject 40, and/or other subjects.

In some embodiments, configuration management component 30 is configured to automatically setting and/or adjusting an activity goal associated with the first subject and/or the second subject based on the equivalent effort factor exceeding a predetermined threshold. For example, responsive to the equivalent effort parameter exceeding 1.5 for first subject 38, configuration management component 30 is configured to lower the activity goal for first subject 38. In some embodiments, configuration management component 30 is configured to automatically set and/or adjust an activity goal associated with first subject 38 and/or the second subject 40 based on a comparison of the second effort parameter and a product of the equivalent effort parameter and the first effort parameter. For example, responsive to second subject 40 reaching a predetermined threshold of the goal, configuration management component 30 may adjust the goal for first subject 38 such that first subject 38's progress toward to the goal is similar to second subject 40's progress.

In some embodiments, configuration management component 30 is configured to create a virtual competitor whose abilities are adapted to first subject 38. In some embodiments, the virtual competitor's performance is based on the first subject's own achievements. In some embodiments, configuration management component 30 is configured to present a challenging target that appears to first subject 38 as achievable.

In some embodiments, configuration management component 30 is configured to cause, via presentation component 32 (described below), a modification to a configuration of the patient interface computer system in response to first subject's progress toward the target. For example, the patient interface computer system may include a wearable device (e.g., a smart watch or other wearable device, etc.). Configurations of the wearable system to be modified may include notifications, one or more types of notifications (e.g., alarms, reminders, etc.), a frequency of notifications (e.g., hourly, six times, four times, or twice daily, etc.), presenting or hiding one or more options from a user interface associated with the wearable device, and/or other configurations. In some embodiments, configuration management component 30 may be configured to, responsive to first subject 38 meeting the target and achieving a better performance than the virtual competitor, cause the wearable device to provide a praise and/or congratulatory message. In some embodiments, responsive to first subject 38 not meeting the target, configuration management component 30 may increase a number of user interface options associated with the wearable device. For example, user interface options corresponding to (i) other activities (that may be more preferable to first subject 38), (ii) instructions for recovery (breathing techniques, slow exercise options), (iii) prompts for entry of subjective data, and/or other options may be presented. In some embodiments, responsive to first subject 38 reaching the target, configuration management component 30 may reduce, limit, or hide one or more user interface options associated with the wearable device.

In some embodiments, configuration management component 30 is configured to determine an activity target at least partially based on simple fartlek (speed play) principles. For example, the activity goals may be randomly increased or decreased during one or more time intervals.

In some embodiments, configuration management component 30 is configured to determine an activity target at least partially based on the "boss-fight" principle of gamification. For example, it may be motivating for first subject 38 to occasionally attempt an activity that is known to be almost impossible without feeling a sense of failure if the goal is not achieved. In this example, first subject 38 may be aware, in advance, that the goal is intended to be a bigger challenge than usual.

In some embodiments, configuration management component 30 may be and/or include a prediction model. As an example, the prediction model may include a neural network or other prediction model (described above) that is trained and utilized for determining and/or adjusting an activity goal (described above). In some embodiments, configuration management component 30 may adjust the activity goal for first subject 38 based on historical and live data corresponding to the one or more physiological measurements associated with first subject 38. For example, first subject 38 may set an activity goal for running (e.g., preparing for a 6 hour marathon). In this example, configuration management component 30 may adjust the marathon finishing time based on first subject 38's previous performance in connection with similar activities (e.g., walking, running, jogging) and/or other activities. In some embodiments, configuration management component 30 may adjust the marathon training pace based on the one or more physiological measurements associated with first subject 38.

In some embodiments, configuration management component 30 may determine different activities associated with the first effort parameter, the second effort parameter, and/or other parameters. For example, configuration management component 30 may (i) substitute cycling for walking or (ii) incline a treadmill and facilitate first subject 38 to choose the desired speed instead of increasing the target speed.

Figure 3:
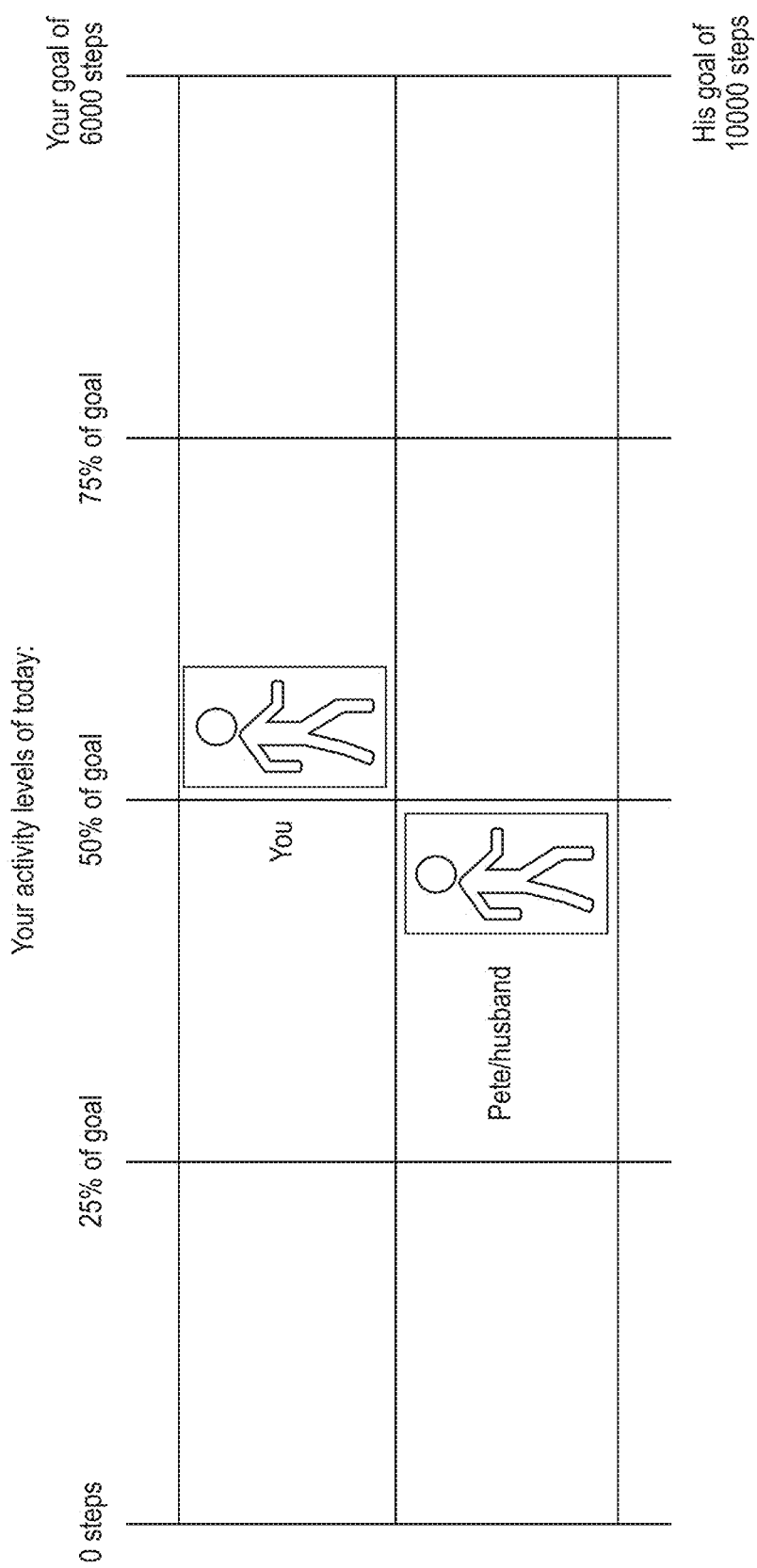
FIG. 3 illustrates a normalized visualization of cooperative activity achievements, in accordance with one or more embodiments.

Presentation component 32 is configured to effectuate, with user interface 20, a progress toward an activity goal associated with first subject 38 based on the equivalent effort parameter. In some embodiments, presentation component 32 is configured to effectuate, via user interface 20, presentation of a normalized visualization of cooperative activity achievements. By way of a non-limiting example, FIG. 3 illustrates a normalized visualization of cooperative activity achievements, in accordance with one or more embodiments. As shown in FIG. 3, presentation component 32 effectuates presentation of a comparison of retrospective progress toward an activity goal for first subject 38 (e.g., based on the equivalent effort parameter) and second subject 40 (e.g., based on the second effort parameter). In some embodiments, presentation component 32 is configured to effectuate presentation of a comparison of real-time progress toward the activity goal for first subject 38 and second subject 40. As such, presentation component 32 is configured to effectuate, via user interface 20, presentation of the equivalent effort factor, the first effort parameter and the second effort parameter during the first time period (e.g., such that acquisition of the one or more physiological measurements associated with first subject 38 and second subject 40 is performed at the same time or during a same period as presentation of the equivalent effort factor, the first effort parameter and the second effort parameter). For example, responsive to first subject 38 exercising regularly with second subject 40 (e.g., a patient and his/her spouse going on daily runs), presentation component 32 is configured to effectuate presentation of real-time equivalent effort parameter and the second effort parameter to first subject 38. In this example, communications component 26 is configured to obtain real-time one or more first measurements and real-time second measurements; effort determination component 28 is configured to determine real-time (i) first effort parameter, (ii) second effort parameter, and (iii) equivalent effort factor based on the real-time data obtained by communications component 26; and presentation component 32 is configured to effectuate presentation of real-time equivalent effort factor, first effort parameter, and the second effort parameter to first subject 38 and/or second subject 40.

In some embodiments, presentation component 32 is configured to effectuate visualizations in a normalized manner. In some embodiments, normalized visualizations display progress when (i) first subject 38 regularly exercises with the same person (e.g., second subject 40) and/or (ii) first subject 38, second subject 40, and/or other subjects have shared goals and/or monitoring. By way of a non-limiting example, the normalized visualization includes raising a structure (tree or a tower of blocks) together. In this example, the structure grows tall and straight only if (normalized) activities levels are balanced. Imbalance in activity levels appear as bends and curves in the structure. As another example, the normalized visualization includes maintaining an environment (e.g., a landscape with different elements) together (e.g., with the family or fellow patients in pulmonary rehabilitation). In this example, each member is responsible for one factor of the landscape (e.g., the rain, sun, grass, bees, etc.). Furthermore, in this example, it may only rain when there's enough (normalized) physical activity.

Figure 4:
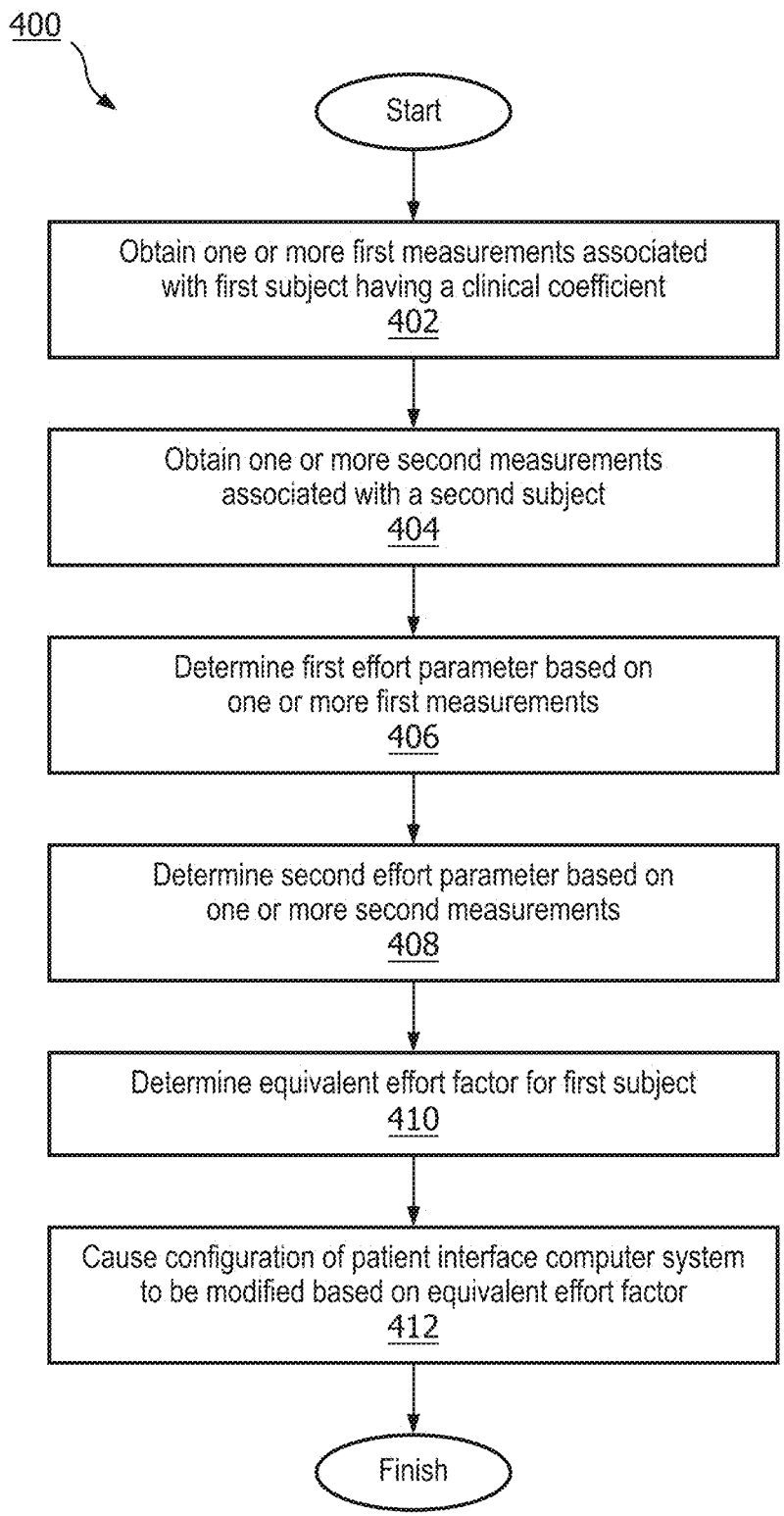
FIG. 4 illustrates a method for facilitating configuration modifications for a patient interface computer system based on an equivalent effort parameter, in accordance with one or more embodiments.

FIG. 4 illustrates a method 400 for facilitating configuration modifications for a patient interface computer system based on an equivalent effort parameter. Method 400 may be performed with a system. The system comprises one or more processors, or other components. The processors are configured by machine readable instructions to execute computer program components. The computer program components include a communications component, an effort determination component, a configuration management component, a presentation component, or other components. The operations of method 400 presented below are intended to be illustrative. In some embodiments, method 400 may be accomplished with one or more additional operations not described, or without one or more of the operations discussed. Additionally, the order in which the operations of method 400 are illustrated in FIG. 4 and described below is not intended to be limiting.

In some embodiments, method 400 may be implemented in one or more processing devices (e.g., a digital processor, an analog processor, a digital circuit designed to process information, an analog circuit designed to process information, a state machine, or other mechanisms for electronically processing information). The devices may include one or more devices executing some or all of the operations of method 400 in response to instructions stored electronically on an electronic storage medium. The processing devices may include one or more devices configured through hardware, firmware, or software to be specifically designed for execution of one or more of the operations of method 400.

At an operation 402, one or more first measurements associated with a first subject are obtained. In some embodiments, the first subject has a clinical coefficient. In some embodiments, operation 402 is performed by a processor component the same as or similar to communications component 26 (shown in FIG. 1 and described herein).

At an operation 404, one or more second measurements associated with a second subject are obtained. In some embodiments, operation 404 is performed by a processor component the same as or similar to communications component 26 (shown in FIG. 1 and described herein).

At an operation 406, a first effort parameter is determined based on the one or more physiological measurements associated with the first subject. In some embodiments, operation 406 is performed by a processor component the same as or similar to effort determination component 28 (shown in FIG. 1 and described herein).

At an operation 408, a second effort parameter is determined based on the one or more physiological measurements associated with the second subject. In some embodiments, operation 408 is performed by a processor component the same as or similar to effort determination component 28 (shown in FIG. 1 and described herein).

At an operation 410, an equivalent effort factor for the first subject is determined based on the one or more first measurements, the one or more second measurements, and the clinical coefficient. In some embodiments, the equivalent effort parameter is indicative of a translation of the first effort parameter to the second effort parameter. In some embodiments, operation 410 is performed by a processor component the same as or similar to effort determination component 28 (shown in FIG. 1 and described herein).

At an operation 412, a configuration of the patient interface computer system is caused to be modified based on the equivalent effort factor. In some embodiments, operation 412 is performed by a processor component the same as or similar to configuration management component 30 (shown in FIG. 1 and described herein).

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. A system configured to facilitate configuration modifications for a patient interface computer system based on an equivalent effort parameter, the system comprising:
one or more processors configured by machine-readable instructions to:
obtain one or more first measurements associated with a first subject with one or more first sensors, the one or more first sensors being configured to provide real-time signals conveying information indicating one or more physiological measurements of the first subject, the first subject having a clinical coefficient;
obtain one or more second measurements associated with a second subject with one or more second sensors, the one or more second sensors being configured to provide real-time signals conveying information indicating one or more physiological measurements of the second subject;
determine a first effort parameter indicative of an exertion level of the first subject based on the one or more first measurements associated with the first subject;
determine a second effort parameter indicative of an exertion level of the second subject based on the one or more second measurements associated with the second subject;
determine an equivalent effort factor for the first subject based on the one or more first measurements associated with the first subject, the one or more second measurements associated with the second subject, and the clinical coefficient, the equivalent effort parameter being indicative of a translation of the first effort parameter to the second effort parameter, the translation enabling quantification of the exertion level of the first subject in terms of the exertion level of the second subject; and cause a configuration of the patient interface computer system to be modified based on the equivalent effort factor.

2. The system of claim 1, wherein the one or more processors are configured to (i) obtain the one or more first measurements and the one or more second measurements during a first time period and (ii) effectuate, via a user interface, presentation of the equivalent effort factor, the first effort parameter and the second effort parameter during the first time period.

3. The system of claim 1, wherein the one or more processors are configured such that determining the equivalent effort factor comprises determining a product of the clinical coefficient and a quotient of the first effort parameter and the second effort parameter.

4. The system of claim 1, wherein the one or more first measurements associated with the first subject and/or the one or more second measurements associated with the second subject include one or more of a heart rate, a breathing rate, a heart rate percentage, a heart rate reserve, a calorie expenditure, a blood oxygen saturation level, maximum volume of oxygen, a number of steps taken, or cardiac cycle, and wherein the equivalent effort factor is one or more of a Metabolic Equivalent of Task (MET), a Training Impulse (TRIMP), a fraction of maximal heart rate, a fraction of heart rate reserve, an energy expenditure, or a Borg scale of perceived exertion.

5. The system of claim 1, wherein causing a configuration of the patient interface computer system to be modified includes automatically setting and/or adjusting an activity goal associated with the first subject and/or the second subject based on the equivalent effort factor exceeding a predetermined threshold.

6. A method for facilitating configuration modifications for a patient interface computer system based on an equivalent effort parameter with a system, the system comprising one or more processors, the method comprising:

obtaining one or more first measurements associated with a first subject with one or more first sensors, the one or more first sensors being configured to provide real-time signals conveying information indicating one or more physiological measurements of the first subject, the first subject having a clinical coefficient;

obtaining one or more second measurements associated with a second subject with one or more second sensors, the one or more second sensors being configured to provide real-time signals conveying information indicating one or more physiological measurements of the second subject;

determining, with the one or more processors, a first effort parameter indicative of an exertion level of the first subject based on the one or more first measurements associated with the first subject;

determining, with the one or more processors, a second effort parameter indicative of an exertion level of the second subject based on the one or more second measurements associated with the second subject;

determining, with the one or more processors, an equivalent effort factor for the first subject based on the one or more first measurements associated with the first subject, the one or more second measurements associated with the second subject, and the clinical coefficient, the equivalent effort parameter being indicative of a translation of the first effort parameter to the second effort parameter, the translation enabling quantification of the exertion level of the first subject in terms of the exertion level of the second subject; and causing, with the one or more processors, a configuration of the patient interface computer system to be modified based on the equivalent effort factor.

7. The method of claim 6, further comprising (i) obtaining the one or more first measurements and the one or more second measurements during a first time period and (ii) effectuating, via a user interface, presentation of the equivalent effort factor, the first effort parameter and the second effort parameter during the first time period.

8. The method of claim 6, wherein determining the equivalent effort factor comprises determining a product of the clinical coefficient and a quotient of the first effort parameter and the second effort parameter.

9. The method of claim 6, wherein the one or more first measurements associated with the first subject and/or the one or more second measurements associated with the second subject include one or more of a heart rate, a breathing rate, a heart rate percentage, a heart rate reserve, a calorie expenditure, a blood oxygen saturation level, maximum volume of oxygen, a number of steps taken, or cardiac cycle, and wherein the equivalent effort factor is one or more of a Metabolic Equivalent of Task (MET), a Training Impulse (TRIMP), a fraction of maximal heart rate, a fraction of heart rate reserve, an energy expenditure, or a Borg scale of perceived exertion.

10. The method of claim 6, wherein causing a configuration of the patient interface computer system to be modified includes automatically setting and/or adjusting an activity goal associated with the first subject and/or the second subject based on the equivalent effort factor exceeding a predetermined threshold.

11. A system configured to facilitate configuration modifications for a patient interface computer system based on an equivalent effort parameter, the system comprising:

means for obtaining one or more first measurements associated with a first subject, the means for obtaining the one or more first measurements being configured to provide real-time signals conveying information indicating one or more physiological measurements of the first subject, the first subject having a clinical coefficient;

means for obtaining one or more second measurements associated with a second subject, the means for obtaining the one or more second measurements being configured to provide real-time signals conveying information indicating one or more physiological measurements of the second subject;

means for determining a first effort parameter indicative of an exertion level of the first subject based on the one or more first measurements associated with the first subject;

means for determining a second effort parameter indicative of an exertion level of the first subject based on the one or more second measurements associated with the second subject;

means for determining an equivalent effort factor for the first subject based on the one or more first measurements associated with the first subject, the one or more second measurements associated with the second subject, and the clinical coefficient, the equivalent effort parameter being indicative of a translation of the first effort parameter to the second effort parameter, the translation enabling quantification of the exertion level of the first subject in terms of the exertion level of the second subject; and means for causing a configuration of the patient interface computer system to be modified based on the equivalent effort factor.

12. The system of claim 11, further comprising (i) means for obtaining the one or more first measurements and the one or more second measurements during a first time period and (ii) means for effectuating presentation of the equivalent effort factor, the first effort parameter and the second effort parameter during the first time period.

13. The system of claim 11, wherein the means for determining the equivalent effort factor comprises means for determining a product of the clinical coefficient and a quotient of the first effort parameter and the second effort parameter.

14. The system of claim 11, wherein the one or more first measurements associated with the first subject and/or the one or more second measurements associated with the second subject include one or more of a heart rate, a breathing rate, a heart rate percentage, a heart rate reserve, a calorie expenditure, a blood oxygen saturation level, maximum volume of oxygen, a number of steps taken, or cardiac cycle, and wherein the equivalent effort factor is one or more of a Metabolic Equivalent of Task (MET), a Training Impulse (TRIMP), a fraction of maximal heart rate, a fraction of heart rate reserve, an energy expenditure, or a Borg scale of perceived exertion.

15. The system of claim 11, wherein the means for causing a configuration of the patient interface computer system to be modified includes means for automatically setting and/or adjusting an activity goal associated with the first subject and/or the second subject based on the equivalent effort factor exceeding a predetermined threshold.

* * * * *